Figure 1:
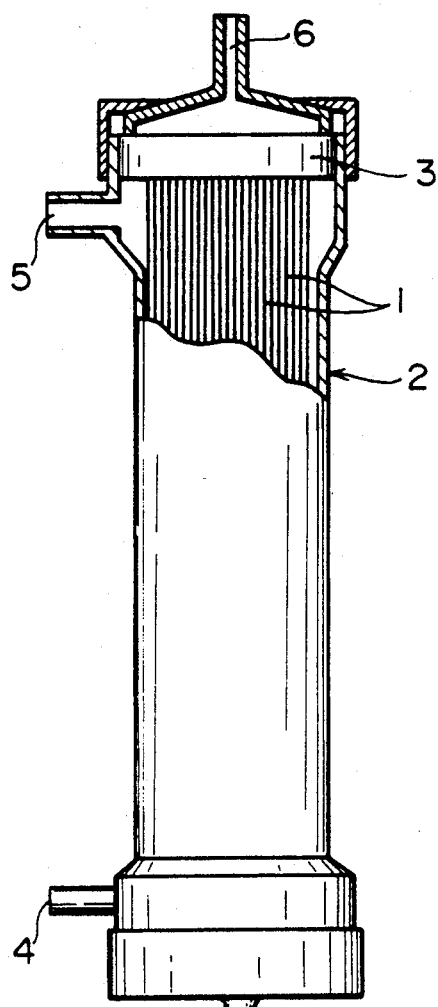

United States Patent [19]
Anazawa et al.

[11] Patent Number: 5,254,143
[45] Date of Patent: Oct. 19, 1993

[54] DIAPHRAGM FOR GAS-LIQUID CONTACT, GAS-LIQUID CONTACT APPARATUS AND PROCESS FOR PRODUCING LIQUID CONTAINING GAS DISSOLVED THEREIN

[75] Inventors: Takanori Anazawa, Sakura; Hideki Watanabe, Chiba, both of Japan

[73] Assignee: Dainippon Ink and Chemical, Inc., Tokyo, Japan

[21] Appl. No.: 970,957

[22] Filed: Nov. 3, 1992

Related U.S. Application Data

[63] Continuation of Ser. No. 727,419, Jul. 9, 1991, abandoned.

[30] Foreign Application Priority Data

Jul. 9, 1990 [JP] Japan .................. 2-180977

[51] Int. Cl.⁵ .................................. B01D 53/22
[52] U.S. Cl. .......................... 95/46; 55/220; 96/6
[58] Field of Search .......... 55/16, 36, 158, 159, 55/189, 80, 84, 220

[56] References Cited

U.S. PATENT DOCUMENTS

| | | | |
|---|---|---|---|
| 1,685,759 | 9/1928 | Walter | 55/16 X |
| 3,210,162 | 10/1965 | Rudd | 55/158 X |
| 3,367,850 | 2/1968 | Johnson | 55/16 X |
| 3,566,580 | 3/1971 | Li | 55/16 |
| 3,651,616 | 3/1972 | Blanchard et al. | 55/16 |
| 3,651,618 | 3/1972 | Klein et al. | 55/16 |
| 3,657,113 | 4/1972 | Stancell et al. | 55/16 X |
| 3,778,971 | 12/1973 | Granger et al. | 55/159 |
| 4,080,288 | 3/1978 | Pilson | 55/16 X |
| 4,268,279 | 5/1981 | Shindo et al. | 55/16 |
| 4,459,139 | 7/1984 | von Reis et al. | 55/159 X |
| 4,473,473 | 9/1984 | Cheng | 55/16 X |
| 4,483,694 | 11/1984 | Takamura et al. | 55/16 X |
| 4,516,984 | 5/1985 | Warner et al. | 55/16 |
| 4,564,373 | 1/1986 | Schmitz et al. | 55/16 |
| 4,775,474 | 10/1988 | Chau et al. | 55/16 X |
| 4,824,444 | 4/1989 | Nomura | 55/16 |
| 4,960,520 | 10/1990 | Semmens | 55/16 X |
| 4,985,055 | 1/1991 | Thorne et al. | 55/159 X |
| 4,986,837 | 1/1991 | Shibata | 55/159 X |
| 5,019,140 | 5/1991 | Bowser et al. | 55/159 |
| 5,037,554 | 8/1991 | Nomi | 55/16 X |
| 5,053,060 | 10/1991 | Kopf-Sill et al. | 55/16 |

FOREIGN PATENT DOCUMENTS

| | | |
|---|---|---|
| 0323341 | 5/1989 | European Pat. Off. . |
| 0420765 | 4/1991 | European Pat. Off. . |
| 63-258605 | 10/1988 | Japan .................. 55/159 |
| WO85/00985 | 3/1985 | PCT Int'l Appl. . |

*Primary Examiner*—Robert Spitzer
*Attorney, Agent, or Firm*—Sherman and Shalloway

[57] ABSTRACT

A diaphragm for gas-liquid contact comprising a membrane having two surfaces, at least one surface of the membrane is hydrophilic and surfaces of micropores present in the membrane are hydrophobic. The diaphragm is used in contact apparatus in which a liquid is contacted with the hydrophilic surface of the membrane and a gas is contacted with the other surface. The diaphragm is used in a process for producing a liquid containing a gas dissolved therein, which comprises introducing a liquid into contact with the hydrophilic surface of the membrane and a gas into contact with the other surface of the membrane and having the gas pass through the membrane and dissolve in the liquid.

25 Claims, 1 Drawing Sheet

DIAPHRAGM FOR GAS-LIQUID CONTACT, GAS-LIQUID CONTACT APPARATUS AND PROCESS FOR PRODUCING LIQUID CONTAINING GAS DISSOLVED THEREIN

This application is a continuation of application Ser. No. 07/727,419, filed Jul. 9, 1991, now abandoned.

This invention relates to a diaphragm for gas-liquid contact wherein a gas and a liquid are contacted via a membrane to dissolve the gas into the liquid, to release the gas or volatiles contained in the liquid, or to conduct the dissolution and the release at the same time; an apparatus using same; and a process for producing a liquid containing a gas dissolved therein by using same. Above all, this invention relates to a diaphragm and an apparatus in which a gas is dissolved in a liquid with good efficiency. The term "gas" in the specification and claims means a vapor too.

This invention can be utilized in the fields of e.g., feeding oxygen into a culture solution in cultivation of microorganisms in drug and food industries, releasing a carbon dioxide gas from the culture solution, feeding oxygen into a waste water in the waste water treatment by aerobic bacteria, releasing a carbon dioxide gas from the waste water, dissolving air into a suspension in floating separation of the suspension under pressure or ore dressing by floatation, oxidizing with air or oxygen in chemical or drug industries, feeding oxygen into water or brine in breeding of fish or transportation of fish, removing $CO_2$, $NO_x$, $SO_x$, $H_2S$, etc., from an exhaust gas and removing $CO_2$ from a fermented methane gas.

A membrane-type gas-liquid contact method is that a gas and a liquid are contacted via a membrane to conduct some materials exchange between the gas and the liquid, such as dissolution of the gas into the liquid or removal of the gas or volatiles dissolved in the liquid into the gas side. In this method, it is necessary that the diaphragm for gas-liquid contact passes a gas but does not pass a liquid. As a homogeneous membrane (nonporous membrane), a silicone resin homogeneous membrane (DE 1,544,037) is known; as a hydrophobic porous membrane, a polypropylene porous membrane (U.S. Pat. 4,268,279), a polyethylene porous membrane (ibid), a polyvinylidene fluoride porous membrane (ibid), a polytetrafluoroethylene porous membrane (H. Yasuda, et al., Journal of Applied Polymer Science, 16, 595–601 (1972)), and apoly-4-methylpentene-1 porous membrane (Japanese Laid-open Patent Application No. 264,127/1988) are known; and as a gas separation membrane, a complex membrane comprising a polysulfone porous membrane and a silicone resin coated thereon (H. Yasuda, et al, Journal of Applied Polymer Science, 16, 595-601 (1972)), and a poly-4-methylpentene-1 heterogeneous membrane (U.S. Pat. No. 4,664,681) are known.

The porous membranes of the above examples, however, have micropores penetrating both sides thereof. Consequently, when a liquid is an organic liquid having low surface tension or a pressure difference between both sides of the membranes is high, the liquid permeates the membranes and leaks in the gas side, so that the membranes cannot be used as the diaphragm for gas-liquid contact.

It is already known that when a hydrophobic porous membrane for microfiltration or ultrafiltration is rendered hydrophilic, a flux improves (e.g., Japanese Laid-open Patent Application No. 133,102/1986). In such a membrane, however, not only the surface but also the inside of the micropore has been rendered hydrophilic; therefore, a liquid such as water permeates the membrane which cannot be actually used as a diaphragm for gas-liquid contact.

As the membrane-type gas-liquid contact apparatus, there are an apparatus in which a gas is dissolved in a liquid, an apparatus in which a gas and volatiles dissolved in a liquid are removed or recovered, an apparatus in which dissolution and removal are conducted at the same time, and an apparatus in which a specific gas is selectively dissolved, removed or recovered.

However, when dissolving a gas into a liquid by the membrane-type gas-liquid contact apparatus or when removing or recovering the gas dissolved in the liquid, bubbles sometimes occur on the surface of the membrane in contact with the liquid. Occurrence of bubbles is drastically observed when employing the hydrophobic porous membrane as a diaphragm and using the gas under pressure. For instance, in case of the polypropylene porous membrane, when a gas pressure is higher than a liquid pressure by about 1 $kgf/cm^2$ or more, a gas is formed as bubbles in an amount of about 100 times to 1,000,000 times the amount of the gas dissolved in the liquid.

Accordingly, it gives rise to disadvantages that a compressor of a large capacity is required, and not only a power cost is increased, but also a mechanism for recycling a gas and raising a rate of absorption is needed. Moreover, occurrence of bubbles in the liquid leads to demerits that a degassing valve has to be installed; as the membrane is covered with the bubbles, the effective area of the membrane in contact with the gas is reduced to decrease the efficiency of dissolving or removing the gas; and the liquid is excessively stirred by the gas (which prevents oxygen from being fed to the cell culture solution).

For the foregoing reasons, the membrane-type gas-liquid contact apparatus is extremely restricted in operating conditions to prevent occurrence of bubbles, so that the performance is low and the usage is limited.

It is an object of this invention to provide a diaphragm for gas-liquid contact, a membrane-type gas-liquid contact apparatus, and a process for producing a liquid containing a gas dissolved therein, in which the gas can efficiently be dissolved in the liquid without occurrence of bubbles even at an elevated gas pressure using the membrane-type gas-liquid contact method.

The object of this invention can be achieved by a diaphragm for gas-liquid contact in this invention characterized in that at least one surface of the membrane is hydrophilic and the surfaces of the micropores present in the membrane are hydrophobic; a membrane for gas-liquid contact in this invention characterized in that at least one surface of a homogeneous membrane or an independent foam membrane is hydrophilic; a membrane-type gas-liquid contact apparatus in this invention wherein these membranes are used as diaphragms, and a liquid is contacted with the hydrophilic surfaces of the membranes; and a process for producing a liquid containing a gas dissolved therein by using the apparatus.

As the membrane of this invention, any membrane will do if one surface or both surfaces are hydrophilic and the surfaces of the micropores present in the membrane are hydrophobic.

First of all, it is explained that the diaphragm is a porous membrane having many micropores that penetrate both surfaces of the membrane.

The porous membrane-type diaphragm for gas-liquid contact in this invention is one in which micropores penetrating both surfaces of the membrane are provided, one or both surfaces of the membrane are hydrophilic, the surfaces of the micropores are hydrophobic, and a liquid is not entered into the micropores nor leaks into the gaseous phase via the micropores.

The "surface of the membrane" here referred to means a front or back surface of the membrane, and when the membrane is a hollow fiber membrane or a tubular membrane, an outer or inner surface thereof. The "surfaces of the micropores" means surfaces of through holes present in the membrane. The "hydrophobic" means that a forward contact angle with water is 90° or more. The "hydrophilic" means that a contact angle with water (static angle) is less than 90°.

When the gas is dissolved in the liquid by the membrane-type gas dissolving method, it is advantageous to raise a gas pressure in order to increase a rate at which to dissolve the gas, i.e., increase a treating amount of the gas-liquid contact apparatus and raise the concentration of the gas dissolved in the liquid. Nevertheless, when the liquid is kept at a normal pressure and the gas pressure is progressively increased, the gas is first dissolved in the liquid where the bubbles do not occur, but small amounts of bubbles then occur on the surface of the membrane, and at last the bubbling state appears in which large amounts of bubbles are formed. Even in the bubbling state in which bubbles occur, it is possible to dissolve the gas into the liquid. However, such inconveniences are unescapable that compared to a state where bubbles substantially do not occur, a rate of dissolution of a gas decreases and an undissolved gas being discarded occurs.

There are differences between the hydrophobic surface and the hydrophilic surface of the membrane with respect to the pressure at which to generate small amounts of bubbles and the pressure at which to allow the bubbling state. Namely, when the surface of the membrane is hydrophobic, the pressure is low. For example, in case of the polypropylene porous membrane, when the pressure difference exceeds 0.1 kgf/cm$^2$, occurrence of small amounts of bubbles is observed. The bubbles are generated even when the concentration of the gas in the. liquid is not saturated. With the pressure difference of 0.3 to 0.5 kgf/cm$^2$, the bubbling state is provided. Meanwhile, when the surface of the membrane is hydrophilic, the bubbling state is not provided until the pressure difference is 2 kgf/cm$^2$, although it depends on the hydrophilic nature of the membrane surface or the diameter of the micropores formed in the membrane surface. Moreover, small amounts of bubbles occurring below the pressure at which to allow the bubbling state are notably reduced. It is advisable that the higher the hydrophilic nature of the membrane surface (the smaller the contact angle) or the smaller the diameter of the micropores formed in the membrane surface at the liquid side, the greater the difference between the gas pressure and the liquid pressure. The contact angle between water and the membrane surface rendered hydrophilic in this invention is 90° or less, preferably 60° or less, more preferably 30° or less, most preferably zero.

When the surfaces of the micropores in the diaphragm for gas-liquid contact are hydrophilic, the liquid enters the insides of the micropores and the micropores are thus filled with the liquid, notably decreasing an exchange rate of the gas. When the liquid pressure is higher than the gas pressure, the liquid leaks into the gas, and the membrane does not act as a diaphragm. The leakage of the liquid occurs both when the gas higher than the liquid pressure and when the gas pressure is in the non-stationary start-up state, with the result that the membrane having the micropores with the hydrophilic surfaces is substantially unusable.

The membrane of this invention is such a membrane that water does not leak into the gas side through the micropores on condition that the water pressure is approximately the same as, or slightly higher than, the gas pressure (e.g., 0.05 kgf/cm$^2$). Namely, as is understandable at once from the knowledge of the surface tension, the forward contact angle between the surfaces of the micropores of this membrane and water exceeds 90°.

As the membrane material of this invention, a hydrophobic material is taken. The hydrophobic material is desirous as the material of the membrane of this invention because the surfaces of the micropores usually are hydrophobic. Examples of the hydrophobic material include polyolefins such as polypropylene, polyethylene and poly-4-methylpentene-1; fluorine resins such as polyvinylidene fluoride and polytetrafluoroethylene; chlorine-containing resins such as polyvinyl chloride and polyvinylidene chloride; silicone resins; polysulfone; and polyphenylene sulfide.

Moreover, a hydrophilic (a contact angle with water is less than 90°) material or a less hydrophobic material is also available as the membrane of this invention by rendering the surfaces of the micropores hydrophobic (water repelling treatment). When the hydrophobic nature of the material is higher (i.e., the contact angle is larger), the pressure at which the liquid enters the micropores becomes higher and the use condition is less restricted. However, the pressure at which the liquid enters the micropores is influenced by the diameter of the micropores, and the material whose hydrophobic nature is lower with the smaller diameter is also available. Examples of the material having the lower hydrophobic nature include polyvinylidene chloride, polyethylene terephthalate, polysulfone, polyether sulfone and polyimide. Examples of the hydrophilic material include acetyl cellulose, ethyl cellulose, regenerated cellulose, nylon 66, polyvinyl alcohol, an ethylene-polyvinyl alcohol copolymer, polyacrylic acid and polymethyl methacrylate.

Among the aforesaid materials, polyolefins, fluorine resins, polysulfone, polyether sulfone and polyphenylene sulfide are especially preferable as the material of the membrane of this invention.

The membrane in this invention includes, besides the porous membrane, a heterogeneous or complex membrane comprising a dense layer (nonporous layer) and a porous sublayer, an independent foam membrane having foams which are not linked to each other, and a homogeneous membrane (nonporous membrane) free from micropores or foams. The heterogeneous membrane or the complex membrane is also the same as the microporous membrane even if the liquid is contacted with the membrane surface in which the micropores are formed or with the membrane surface at the dense layer side. That is, in case of the membranes other than the porous membrane, the membrane surface in contact with the liquid is hydrophilic, thereby suppressing occurrence of bubbles; the surfaces of the micropores in the porous sublayer is hydrophobic, so that the micropores are not filled with the liquid even in the long-term use. When the membrane is the independent foam membrane or the nonporous homogeneous membrane, occurrence of bubbles is suppressed because the membrane surface in contact with the liquid is rendered hydrophilic. When the membrane is made of the material that is not swollen with water, the liquid neither permeates the membrane nor is filled in the independent foams inside the membrane even in the long-term use. The "material that is not swollen with water" here referred to means that the weight of the material after dipped in water of 25° C. for 24 hours is increased by 10% or less.

The size of the micropores may be uniform throughout the thickness direction of the membrane or may have a distribution like an asymmetrical membrane In this invention, the size of the micropores is not particularly limited. It is advisable that the size of the pore in the surface in contact with the liquid is 10 micrometers or less as an average diameter. When the size of the micropores is too large, the liquid is liable to enter the micropores even though the surfaces of the micropores are hydrophobic, and the effect of this invention is lost.

The surface of the membrane made of the hydrophobic material is rendered hydrophilic by a known method. Examples of such a method include oxidation treatment with a sulfuric acid solution of potassium bichromate, a sulfuric acid solution of potassium permanganate, an acid solution of hydrogen peroxide, a hypochlorite salt, a perchlorate salt or fuming nitric acid; sulfonation treatment; corona discharge treatment; ozone treatment; fluorine treatment; chlorine treatment; alkali etching treatment; flame treatment; ionic etching treatment; plasma treatment; plasma polymerization; interfacial polymerization in a membrane surface; graft polymerization in a membrane surface; photopolymerization in a membrane surface; and coating of a hydrophilic polymer.

In this invention, it is required that in the treatment of rendering the membrane hydrophilic, only the surface of the membrane is rendered hydrophilic but the surfaces of the micropores are not rendered hydrophilic. To this end, in case of using a liquid treating agent, for example, containing an oxidizing agent or a hydrophilic polymer, the surface of the membrane may be treated such that the treating agent is contacted with the membrane surface alone and does not enter the insides of the micropores. In case of treatment with a gas such as corona discharge treatment, ozone treatment and plasma treatment, an extent of treatment and a treating time may be controlled. Also available is a method in which a membrane having micropores filled with a protecting agent such as a liquid is rendered hydrophilic, and the protecting agent is then removed.

Whether the membrane surface is rendered hydrophilic or not can be ascertained by measuring the contact angle. When the membrane is a fine hollow fiber and hard to measure the contact angle, said contact angle can be measured by a model test wherein a film made of the same material as the membrane is surface-treated under the same conditions. Moreover, that the surfaces of the micropores are not rendered hydrophilic can be determined from the fact that the micropores are not filled with water or water does not leak into the gas under such a test condition that the water pressure is a bit higher than the gas pressure by e.g., 0.05 kgf/cm$^2$. Whether the micropores are filled with water or not can be known by measuring the weight of the membrane or by measuring whether a rate at which to dissolve the gas in water is reduced to less than 30 % in case of the untreated membrane.

The surfaces of the micropores in the membrane are rendered hydrophobic usually by a method of adhering a water repelling agent to the surfaces of the micropores via water repelling treatment. The water repelling agent includes silicone-type and fluorine-type water repelling agents.

The thickness of the membrane used in this invention is not limited in particular if the membrane is available as a diaphragm for gas-liquid contact; it is preferably 5 to 1,000 micrometers. When the membrane is a combination of a substrate such as ceramics or a nonwoven fabric and a polymeric component, the thickness of the substrate is added to the above thickness. The shape of the membrane in this invention is not limited in particular. For example, a flat membrane, a hollow fiber membrane and a tubular membrane are available. The hollow fiber membrane has preferably a diameter of 3 mm or less.

In this invention, the membrane is produced by any method. A wet processing method, a dry processing method, a melt processing method, a sintering method, a method of blending soluble matters and extracting the blend, a blending and stretching method, an electron beam curing method, a radiation curing method, an ultraviolet curing method, a radiation etching method and a PTFE stretching method are taken in case of the porous membrane. A wet processing method, a melt processing method and a heat treatment method of the porous membrane are taken in case of the heterogeneous membrane. A coating method, a spreading on liquid surface method, a laminating method, a co-extruding method, an interfacial polymerization method, a photopolymerization method and a plasma polymerization method are taken in case of the complex membrane. A foaming method, a melt processing method, a sintering method and a blending and stretching method are taken in case of the independent foam membrane.

The membrane-type gas-liquid contact apparatus of this invention is adapted to have a shape and a structure that the liquid is contacted with the hydrophilic membrane surface using the diaphragm for gas-liquid contact of this invention and is accommodated in e.g., a suitable housing. Usually, the gas-liquid contact system is put to practical use by assembling it together with a liquid inlet, a liquid outlet, a gas inlet, a gas outlet and pipings to connect them. However, the membrane-type gas-liquid contact apparatus of this invention does not make the housing inevitable, but the membrane may directly be dipped in the reaction vessel.

The shape of the membrane-type gas-liquid contact apparatus of this invention is not particularly limited. For instance, when the membrane is a flat membrane, it may take a laminated, spiral or pleated shape. When the membrane is a hollow fiber membrane or a tubular membrane, it may take such a shape that a liquid flows outside or inside the membrane.

The membrane-type gas-liquid contact apparatus of this invention can produce a gas-containing liquid by contacting a liquid such as water, or an aqueous solution or dispersion of an organic or inorganic compound to the hydrophilic surface of the diaphragm for gas-liquid contact, contacting a gas such as air, oxygen, nitrogen, carbon dioxide gas or exhaust gas to the other surface of the membrane, and keeping the liquid and/or the gas under normal pressure or elevated pressure. On this occasion, the gas-containing liquid can be produced even at the gas pressure of 0.5 kgf/cm$^2$G or higher substantially without occurrence of bubbles. In this invention, the gas pressure is not particularly limited, but preferably 200 kg/cm$^2$ or lower.

The following Examples and Comparative Examples illustrate this invention more specifically. However, this invention is not limited thereto.

In the attached drawings

Figure 2:
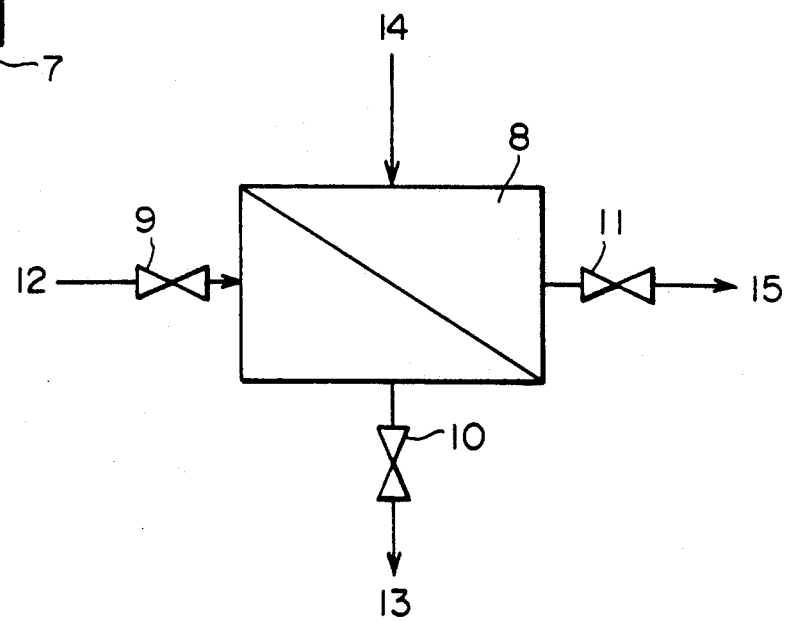

FIG. 1 is a partial longitudinal sectional front view of a membrane-type gas-liquid contact apparatus used in said Examples. FIG. 2 is a diagram of a gas-liquid contacting system used in said Examples.

EXAMPLE 1

A polypropylene porous hollow fiber membrane made by Hochst-Celanese Corp. (outer diameter 400 micrometers, inner diameter 330 micrometers, pore diameter 0.4×0.04 micrometer) was dippped in a conc. sulfuric acid saturated solution of potassium bichromate to make the outer surface of the hollow fiber hydrophilic. On this occasion, the treating solution was contacted with the outer surface of the hollow fiber membrane alone and was not entered into the hollow fiber through the micropores. The contact angle (static angle) with water of the polypropylene film which was oxidized under the same conditions was 95° before treatment and 75° after treatment. Subsequently, as shown in FIG. 1, about 5,000 hollow fiber membranes 1, were sealed inside a housing 2 by a resin 3 to provide a membrane-type gas-liquid contact apparatus 8 having a membrane area of about 1 m$^2$ based on the hollow fiber outer surface. Using said apparatus 8, a gas-liquid contact treating system shown in FIG. 2 was assembled.

The housing 2 of the membrane-type gas-liquid contact apparatus 8 was made of a transparent polycarbonate resin, making it possible to observe the inside. A solution 12 being treated (25° C.) was introduced into a liquid inlet 4 of the apparatus 8. Measurement was first conducted under water pressure of 0.05 kgf/cm$^2$ G. Leakage of water was not observed. Then, a pressure control valve 10 was adjusted such that the pressure in a liquid outlet 5 of a treated water 13 became 2.0 kgf/cm$^2$G, and a flow rate was adjusted to 5.0 liters/min by a flow rate control valve 9. Meanwhile a compressed air 14 of 4.0 kgf/cm$^2$G was introduced into a gas inlet 6, and a leak valve 11 connected to a gas outlet 7 was opened to such an extent that about 0.1 liter/min of an exhaust gas 15 leaked.

A concentration of dissolved oxygen in the water being treated and the treated water was measured by an oxygen concentration meter. As a result, it was found that the water being treated was 8.1 ppm and the treated water was 15.1 ppm. At this time, occurrence of bubbles was not observed in the treated water. Small amounts of bubbles were found in the treated water that flowed out, but they were generated after the treated water passed through the pressure control valve 10.

COMPARATIVE EXAMPLE 1

An apparatus was manufactured as in Example 1 except that the hollow fiber membrane was not rendered hydrophilic. The test was then conducted under the same conditions as in Example 1. It was then observed that bubbles vigorously occurred from the hollow fiber membrane, and air flowed out in a large amount of at least 10 times that of the treated water in volume ratio. Moreover, it was hard to make the pressure constant, and the concentration of dissolved oxygen in the treated water was only 8.4 ppm. When the pressure of air fed was lowered until the large amount of the gas was not formed in the treated water, the air pressure reached 2.2 kgf/cm$^2$ G, and the concentration of dissolved oxygen in the treated water at this time was 11.9 ppm. Further, while keeping the air pressure at 2.2 kgf/cm$^2$G, the flow rate was adjusted such that the concentration of dissolved oxygen in the treated water became 15.1 ppm. Then, the flow rate of the treated water became 2.2 liters/min.

COMPARATIVE EXAMPLE 2

Example 1 was followed except that the hollow fiber membrane was dipped in ethanol, water, conc. sulfuric acid, and a conc. sulfuric acid saturated solution (a treating solution for oxidation) of potassium bichromate.

By the above dipping procedure, the treating solution for oxidation permeated the hollow fiber membrane, and the hollow fiber membrane showing white turned semitransparent in a state dipped in the treating solution for oxidation. From this it follows that the oxidation was carried out such that the treating solution for oxidation was filled in the micropores of the membrane. Moreover, the contact angle of the treated polypropylene film was measured in the same way was measured. As a result, the contact angle before treatment was 95° and that after treatment was 75°. It was therefore found that the surface in contact with the treating solution for oxidation was rendered hydrophilic.

The resulting membrane was tested under the conditions that the air pressure was a normal pressure and the water pressure was 0.05 kgf/cm$^2$G. It was found that water leaked into air. Thus, it became apparent that the membrane rendered hydrophilic up to the surfaces of the micropores does not act as a diaphragm for gas-liquid contact.

EXAMPLE 2

Poly(4-methylpentene-1) having melt index of 26 was melt-spun at a spinning temperature of 290° C. and a draft of 300 to prepare a hollow fiber intermediate. Said intermediate was subjected to heat treatment at a temperature of 210° C. and a draw ratio (DR) of 1.05 for a treating time of 5 seconds, cold drawing at a temperature of 25° C. and DR of 1.2, hot drawing at temperature 150° C. and DR of 1.3, and heat setting at a temperature of 200° C. and DR of 0.9. There was obtained a hollow fiber membrane having an outer diameter of 300 micrometers and an inner diameter of 240 micrometers. When this membrane was observed by a scanning-type electron microscope (SEM), it was found that many micropores having a diameter of about 0.05 micrometer were formed in the inner surface of the hollow fiber membrane and micropores having a pore diameter of about 0.1 micrometer are sparsely formed in the outer surface thereof. When the section of the hollow fiber membrane was observed by SEM, said membrane was found to have a heterogeneous structure comprising a dense layer on the outer surface and a porous sublayer having a pore diameter of about 0.05 micrometer. Said membrane had oxygen permeability of 0.87×10$^{-4}$ (STP)/cm$^2$.sec.cmHg, nitrogen permeability of 0.78×10$^{-4}$ (STP)/cm$^2$.sec.cmHg and an oxygen/nitrogen separation coefficient of 1.12.

This hollow fiber membrane was subjected to corona discharge treatment under a condition of 12.5 w.min/m² by passing through a corona discharge treatment device at a rate of 50 M/min. Then, a membrane-type gas-liquid contact apparatus having a membrane area of about 1 m² based on the hollow fiber outer surface, shown in FIG. 1, was manufactured as in Example 1, and a gas-liquid contact treating system shown in FIG. 2 was assembled. Using the treating system, the leakage test was run by applying the water pressure of 0.05 kgf/cm² G to the membrane-type gas-liquid contact apparatus. Consequently, leakage of water was not observed. Besides, using the treating system, the test was run as in Example 1, and a flow rate at which the concentration of dissolved oxygen in the treated water became 15.1 ppm was 5.2 liters/min. The contact angle (static angle) with water of the poly-4-methylpentene-I film which was subjected to the corona discharge treatment under the same conditions was 105° before treatment and 85° after treatment.

COMPARATIVE EXAMPLE 3

An apparatus was manufactured as in Example 2 except that the hollow fiber membrane was not subjected to corona discharge treatment, and the test was run under the same conditions as in Example 2. It was then observed that bubbles are vigorously generated from the hollow fiber membrane, and together with the treated water, air flowed out in an amount which was approximately the same as the amount of the treated water (by volume ratio). Further, it was hard to make the water pressure constant, and the concentration of dissolved oxygen in the treated water was only 949 ppm. When the pressure of air fed was lowered until bubbles were not generated, the air pressure became 2.3 kgf/cm²G, and the concentration of dissolved oxygen in the treated water was 12.4 ppm when the flow rate was 5.2 liters/min. Still further, while keeping the air pressure at the same 2.3 kgf/cm²G, the flow rate was adjusted such that the concentration of dissolved oxygen in the treated water became 15.1 ppm. Then, the flow rate of the treated water became 2.4 liters/min.

COMPARATIVE EXAMPLE 4

Example 2 was repeated except that the corona discharge treatment of the hollow fiber membrane was carried out under the conditions of 8.3 m/min and 75 w.min/m². The resulting membrane was tested under the conditions that the air pressure was a normal pressure and the water pressure was 0.05 kgf/cm² G. As a result, water leaked into air. It was therefore seen that under these conditions of rendering the membrane hydrophilic, not only the surface of the membrane but also the surfaces of the micropores are rendered hydrophilic and the membrane with the surfaces of the micropores rendered hydrophilic does not act as a diaphragm for gas-liquid contact.

EXAMPLE 3

A hollow fiber membrane was formed under the same conditions as in Example 2 except that DR in the heat treatment was 1.6. By the observation of the resulting membrane via SEM, the micropores were not found on both sides of the hollow fiber membrane. However, when the section of the membrane was subjected to ionic etching and observation via SEM, void cells each having a diameter of 0.05 micrometer were found throughout the surface of-the membrane. The membrane had oxygen permeability of $5.50 \times 10^{-6}$ cm³(STP)/cm². sec.cmHg, nitrogen permeability of $1.28 \times 10^{-6}$ cm(STP)/cm². sec.cmHg and oxygen/nitrogen separation coefficient of 4.3. From the foregoing, the membrane was confirmed to be an independent foam membrane. In the same manner as in Example 2, this membrane was then rendered hydrophilic; using said membrane, a gas-liquid contact treating system was assembled, and the test was likewise performed. In measuring leakage upon applying the water pressure of 0.05 kgf/cm²G, leakage of water was not observed, and a flow rate at which the concentration of dissolved oxygen in the treated water became 15.1 ppm was 4.9 l/min.

In accordance with this invention, as stated and shown above, there is provided a diaphragm for gas-liquid contact which has high contact efficiency because the membrane is free from clogging by bubbles at the liquid side and which can increase a rate of dissolution of a gas by elevating the pressure of the gas. Since the membrane-type gas-liquid contact apparatus of this invention using such a diaphragm such gas-liquid contact can prevent occurrence of bubbles in the liquid, there are merits that a degassing valve need not be installed at the liquid side, there is no loss of the dissolved gas, stirring of the liquid due to bubbles does not occur, a permissible pressure range is wide, and operation is easy to control. In addition, when using the membrane-type gas-liquid contact apparatus of this invention, the gas-containing liquid can be produced with good efficiency without allowing occurrence of bubbles in the liquid.

What we claim is:

1. A process for producing a liquid containing a gas dissolved therein, which comprises introducing a liquid into a hydrophilic side of a diaphragm for gas-liquid contact wherein the diaphragm comprises a single membrane or a laminate of at least two membranes, at least one surface of the membrane is hydrophilic and all surfaces of micropores present in the membrane are essentially hydrophobic, and introducing a gas into the other side of the membrane for gas-liquid contact.

2. The process of claim 1 wherein the gas is a pressurized gas of 0.5 kgf/cm² G or higher.

3. The process of claim 1 for producing a liquid containing a gas dissolved therein wherein the pressure of the gas is higher than the pressure of the liquid by at least 0.5–200 kgf/cm².

4. The process of claim 1 for producing a liquid containing a gas dissolved therein wherein the liquid is water.

5. The process of claim 1 for producing a liquid containing a gas dissolved therein wherein the liquid is water and the gas is air.

6. A diaphragm comprising a single membrane for gas-liquid contact, wherein at least one surface of the membrane is hydrophilic and all surfaces of micropores present in the membrane are essentially hydrophobic, and the thickness of said membrane is 5 to 1,000 micrometers and the micropores are 10 micrometers or less in size.

7. The diaphragm of claim 6 wherein the membrane is a porous membrane having through holes.

8. The diaphragm of claim 6 wherein the membrane is made of a hydrophobic material, the surface of the membrane was treated to make it hydrophilic and the hydrophobic surface of the micropores were not affected by the treatment.

9. The diaphragm of claim 8 wherein the hydrophobic material is a member selected from the group consisting of a poly-propylene, polyethyelen, poly-4-methylpentene-1, polyvinylidene fluoride, polytetrafluoroethylene, polystyrene, polyether sulfone and polyphenylene sulfide.

10. The diaphragm for gas-liquid contact of claim 8 wherein the hydrophobic material is a poly-4-methylpentene-1.

11. A diaphragm-type gas-liquid contact apparatus comprising a single membrane in which at least one surface is hydrophilic and all surfaces of micropores present in the membrane are essentially hydrophobic, and a liquid is contacted with the at least one hydrophilic surface of the membrane, and a gas is contacted with the other surface and the thickness of said membrane is 5 to 1,000 micrometers and the micropores are 10 micrometers or less in size.

12. The apparatus of claim 11 wherein the membrane is a porous membrane having through holes.

13. The apparatus of claim 11 wherein the membrane is made of a hydrophobic material, the surface of the membrane was treated to make it hydrophilic and the hydrophobic surfaces of the micropores were not affected by the treatment.

14. The apparatus of claim 13 wherein the hydrophobic material is a member selected from the group consisting of polypropylene, polyethylene, poly-4-methylpentene-1, polyvinylidene fluoride, polytetrafluoroethylene, polysulfone, polyether sulfone and polyphenylene sulfide.

15. A diaphragm for gas-liquid contact in which the diaphragm membrane is a hollow fiber type heterogeneous membrane or independent foam membrane, wherein the inner surface of said membrane is hydrophilic and all surfaces of micropores present in the membrane are essentially hydrophobic.

16. A membrane-type liquid-gas contact apparatus in which a membrane which is a hollow fiber type heterogeneous membrane or independent foam membrane, wherein the inner surface of said membrane is hydrophilic and all surfaces of micropores present in the membrane are essentially hydrophobic, is used as a diaphragm, and a liquid is contacted with the inner side of said hollow fiber membrane.

17. A membrane-type gas-liquid contact apparatus in which a membrane composed of a membrane, which is a hollow fiber type heterogeneous membrane or independent foam membrane, wherein the inner surface of said membrane is hydrophilic and all surfaces of micropores present in the membrane are essentially hydrophobic, has no housing and is directly dipped in a liquid.

18. A diaphragm for gas-liquid contact comprising a single membrane having two surfaces, said membrane containing micropores which have surfaces extending through said membrane to each of said two surfaces, wherein at least one of the membrane surfaces is hydrophilic and all the micropore surfaces are essentially hydrophobic, said at least one hydrophilic membrane surface is for contact with a liquid and said other membrane surface is for contact with a gas.

19. A method for dissolving a gas in a liquid which comprises introducing a liquid into contact with the at least one hydrophilic membrane surface of the diaphragm of claim 18 and introducing a gas into contact with the other surface of the membrane, said gas passing through said membrane and dissolving in said liquid.

20. A diaphragm for gas-liquid contact comprising a hollow fiber membrane having an inner surface and an outer surface, said membrane containing micropores which have surfaces extending through said membrane to each of said inner and outer surfaces, wherein at least one of the membrane surfaces is hydrophilic and all the micropore surfaces are essentially hydrophobic, said at least one hydrophilic member surface is for contact with a liquid and said other membrane surface is for contact with a gas.

21. The diaphragm of claim 20 wherein the inner fiber membrane surface is hydrophilic and in contact with a liquid and the outer fiber membrane surface is in contact with a gas.

22. The diaphragm of claim 20 wherein the outer fiber membrane surface is hydrophilic and in contact with a liquid and the inner membrane surface is in contact with a gas.

23. A method for dissolving a gas in a liquid which comprises introducing a liquid into contact with the at least one hydrophilic membrane surface of the fiber membrane of claim 20 and introducing a gas into contact with the other surface of the fiber membrane, said gas passing through said fiber membrane and dissolving in said liquid.

24. The method of claim 23 wherein the inner fiber membrane surface is hydrophilic and in contact with the liquid and the outer fiber membrane surface is in contact with the gas.

25. The method of claim 23 wherein the outer fiber membrane surface is hydrophilic and in contact with the liquid and the inner fiber membrane surface is in contact with the gas.

* * * * *